United States Patent [19]
Praeger

[11] Patent Number: 5,782,901
[45] Date of Patent: Jul. 21, 1998

US005782901A

[54] SUTURELESS ELECTRODE CLIP

[76] Inventor: Peter L. Praeger, 877 Longhill Rd. West, Briarcliff Manor, N.Y. 10510

[21] Appl. No.: 843,467

[22] Filed: Apr. 16, 1997

[51] Int. Cl.$^6$ .................................................. A61N 1/05
[52] U.S. Cl. ................................. 607/130; 607/115
[58] Field of Search ........................... 607/130, 115, 607/116, 119; 600/373, 374, 382

[56] References Cited

U.S. PATENT DOCUMENTS 3,999,555  12/1976  Person.
4,144,889  3/1979  Tyers et al..
4,313,448  2/1982  Stokes.
4,351,345  9/1982  Carney.
5,207,691  5/1993  Nardella .......................... 607/115

*Primary Examiner*—Scott M. Getzow
*Attorney, Agent, or Firm*—Cowan, Liebowitz & Latman, P.C.

[57] ABSTRACT

The present invention provides for a sutureless clip for use in temporarily pacing the human heart. The clip comprises a generally V-shaped clip having on at least one outer surface thereof with one or more channels for the attachment of pacing electrodes, the inner surfaces of the clip optimally being textured to provide a greater contact surface area. The clip is readily deformable to allow for its attachment to the outer surface of the heart.

9 Claims, 3 Drawing Sheets

SUTURELESS ELECTRODE CLIP

FIELD OF THE INVENTION

The present invention relates to an apparatus for placing electrodes on the heart. More particularly, the invention relates to a sutureless clip for attaching electrodes to the heart for temporary pacing and a method of doing so.

BACKGROUND OF THE INVENTION

In the course of many surgical procedures involving the heart, a standard procedure in most cardiac centers is, prior to closing the sternum, to connect a temporary pacing device to the heart. This is usually done with a wire which is connected to an external cardiac pacer. The pacing may be accomplished in either a unipolar or bipolar fashion.

Typically, pacing electrode leads are sutured onto the right atrium or ventricular wall. However, problems may arise in pacing and sensing. In many instances there will be bleeding while the leads are placed or removed, which creates an unnecessary complication. Also, the wall may be thin and friable, which adds further complications.

Electrode resistance is a function of the electrode radius such that a higher resistance is provided by a smaller electrode. Stimulation threshold is a function of current density generated at the electrode. The smaller the radius of the electrode, the greater the current density. The resistance at the electrode myocardia interface is higher with smaller electrodes. In contrast, sensing impedance and electrode polarization are decreased with electrodes of larger surface area. These sensing considerations favor the use of a large area electrode.

The ideal pacing lead would have an electrode with a small radius, which serves to increase current density, and a large surface area, which serves to improve sensing ability. It has been found that the best way to provide for these conflicting advantages is to provide an electrode with a small radius and a lead having a complex surface structure that provides a large surface area. Prior pacing leads used electrodes with a polished metal surface. The use of electrodes with a textured surface has resulted in a dramatic increase in the surface area of the electrode without an increase in its radius.

OBJECTS OF THE INVENTION

It is an object of the invention to provide a sutureless electrode clip.

It is also an object of the invention to provide a sutureless electrode clip that quickly and safely fastens to the heart to provide temporary pacing.

It is a further object of the invention to provide a sutureless clip for attachment to the heart when the electrode lead is intended to take advantage of the increased current density resulting from a small radius of the electrode and decreased sensing impedance that is characteristic of a larger surface area.

These are other objects of the invention will be more apparent from the discussion below.

SUMMARY OF THE INVENTION

In accordance with the present invention a sutureless clip for use in connecting a temporary heart pacing device to the epicardium of a human heart is provided. The clip consists of a generally V-shaped clip having on at least one outer surface thereof one or more channels for receiving pacing electrodes to be connected through the skin to a pulse generator, which may be uni- or bipolar. The outer surface and lateral surfaces of the clip have an insulated coating, and, when there are two channels on a surface, there will be an insulating barrier between the two channels. One or more of the non-insulated inner surfaces of the clip are textured to provide a greater contact surface area, and the clip is readily deformable to allow for its attachment to the surface of the heart. The clip is preferably applied with a grasping applicator forceps which is provided with a set of jaws to accommodate the clip geometry, so that the user may insert a clip into the forceps and, by applying pressure to the grasping end of the forceps, deform the clip in a desired position on the surface of the heart.

The clip and grasping forceps system of the present invention has the advantage that no suturing of the pacing leads to the heart is required. This eliminates the disadvantages associated with bleeding which occur when such suturing is carried out and the problems normally encountered when the walls of the heart have become thin and friable.

Furthermore, the clip of the present invention provides a better overall pacing lead connection due to the very large relative contact area provided by the textured inner surfaces of the clip which come in contact with the heart tissue. This contrasts with the usual wire that is used to penetrate the atrium, leaving a very small contact point with the heart.

DESCRIPTION OF THE PREFERRED EMBODIMENT

Figure 1:
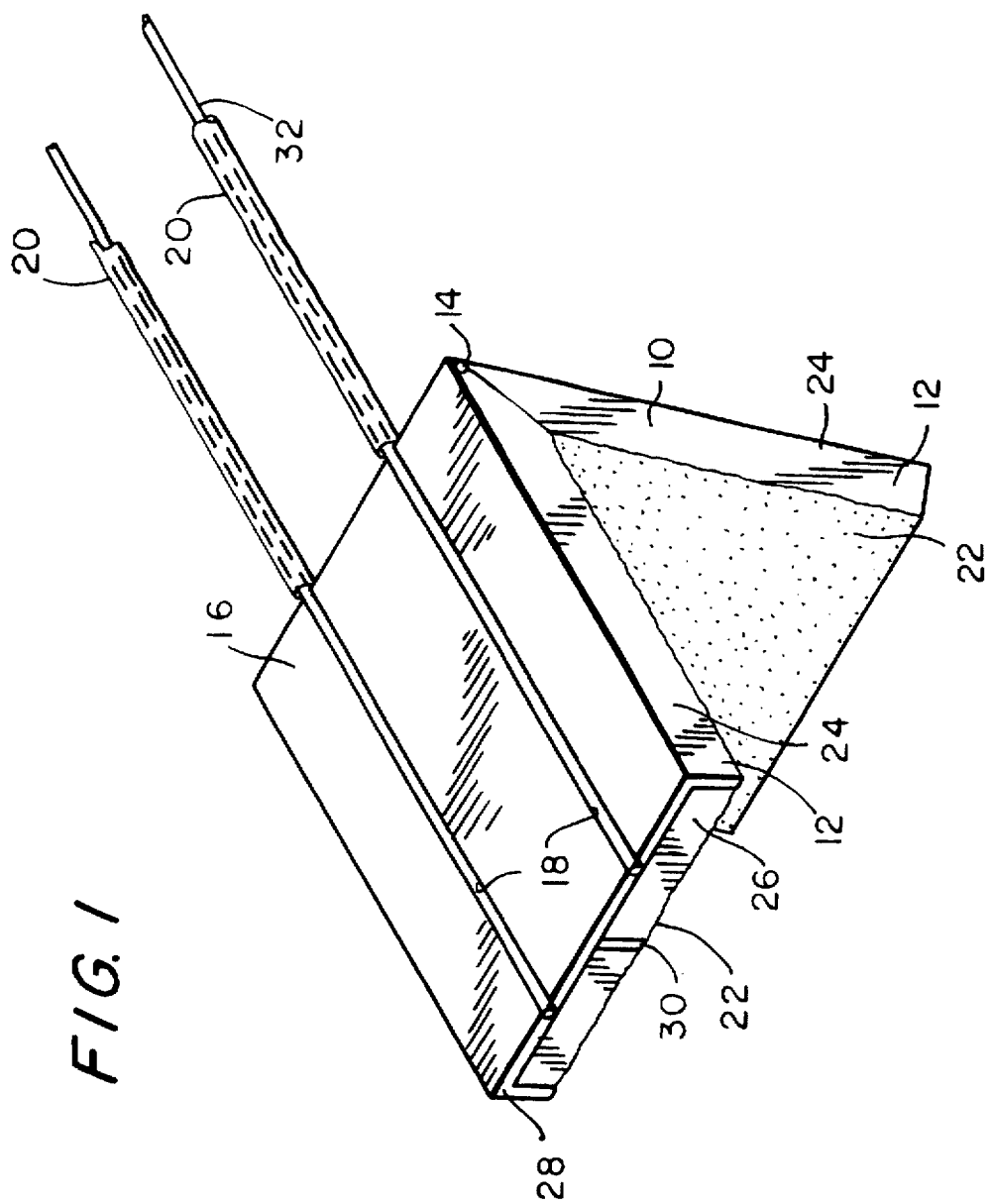
FIG. 1 is a perspective view of the clip of the invention showing the essential components.

In FIG. 1 a perspective view of the sutureless clip of the present invention is depicted showing the V-shaped clip 10, having two jaws 12, which are deformable about an axis 14. The outer surface 16 of at least one of the jaws 12 is provided with at least one channel 18 intended to receive and engage a pacer electrode 20. The inner surface 22 of each jaw 12 is preferably textured to increase the contact surface area.

Figure 2:
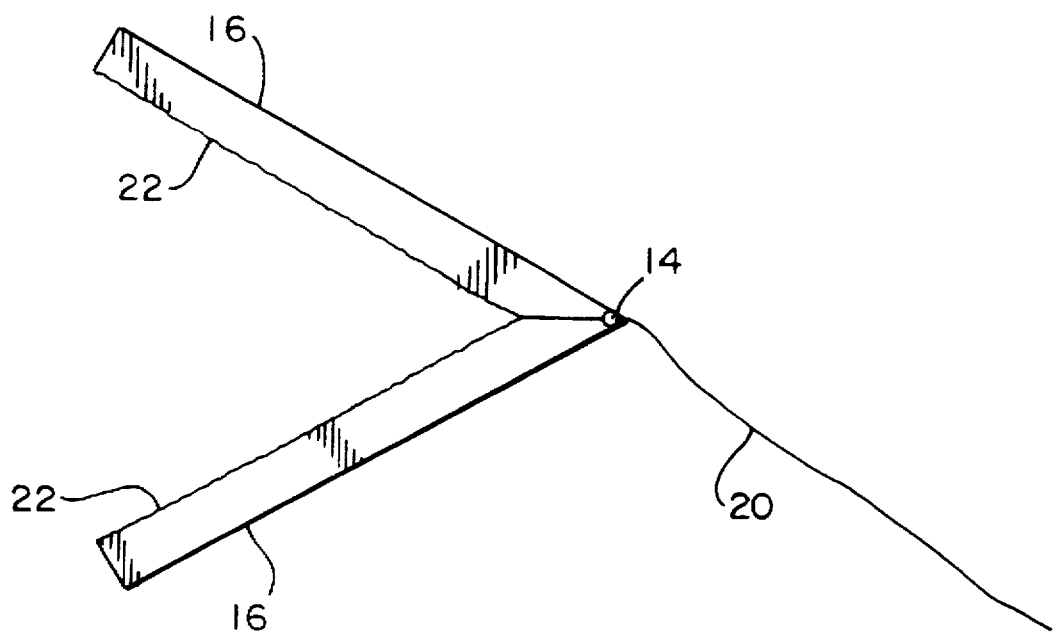
FIG. 2 is a right side view of the clip of FIG. 1.

A lateral view of clip 10 of FIG. 1 is shown in FIG. 2, depicting outer surfaces 16 of each jaw 12, inner textured surfaces 22, pacer electrodes 20, and axis of deformation rotation 14.

The outer surfaces 16, lateral surfaces 24, and, optionally, end surfaces 26 have an insulated layer 28. Layer 28 comprises a physiologically acceptable electrical insulating material, such as a silicone polymer or copolymer. When an outer surface layer 16 has two channels 18, jaws 12 will also comprise an insulating barrier 30. Barrier 30 can be comprised of a physiologically acceptable electrical insulation similar to, or different from, the material of insulating layer 28.

The portion of electrode 20 proximal to clip 10 will have a typical electrical insulation 32. Insulation 32 can comprise any of the known, physiologically acceptable polymers or co-polymers suitable for this purpose.

Figure 3:
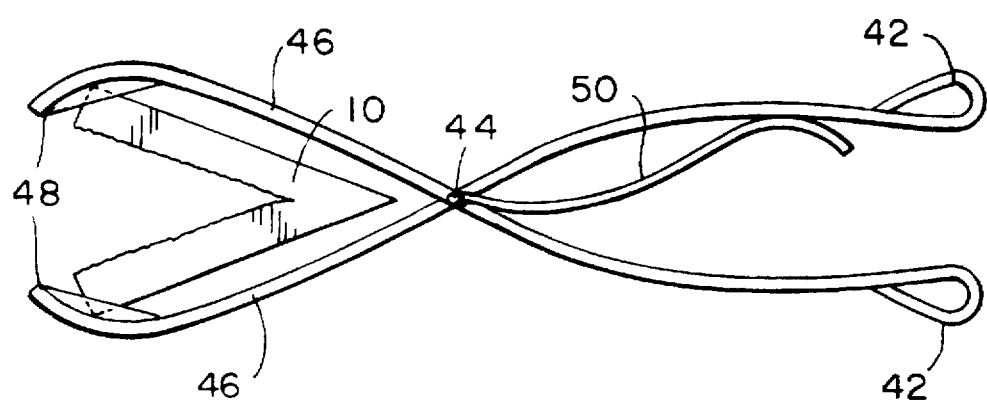
FIG. 3 is a plan view of the grasping forceps used to place the clip of FIG. 1, showing one clip in place prior to placement on the heart.

FIG. 3 is a lateral view of a long-handled, grasping forceps 40 used to place clip 10. Forceps 40 has a pair of elongated grasping handles 42 which are rotatable about an axis or point 44. The grasping ends 46 of forceps 40 are provided with retainer means 48 with which to secure the ends of the clip 10 within the jaws 46, in the open position. Forceps 40 are also provided with a spring means 50, which maintains forceps 40 in the open position until force is applied to forceps handles 42 to position clip 10 and deform it in the desired position on the epicardium.

The clip 10 of the present invention may be fabricated out of any of a number of physiologically acceptable, suitable materials as will be known to one skilled in this art. It has been found that the following materials are particularly useful for fabrication of the V-shaped clip of the invention: platinum, iridium, Elgiloy, pyrolitic, carbon coating, ipanium, graphite platinum and iridium oxide.

The grasping forceps used to place the V-shaped clip of the present invention may be fabricated out of a number of known materials as will be familiar to one skilled in the art of surgical instruments. Typically the grasping forceps of the present invention will be fabricated out of stainless steel or some other metal alloy which have been found to be suitable for surgical applications.

The method of the present invention for attachment of pacing leads to the human heart muscle consists of:

inserting a V-shaped clip into the retaining end of the grasping forceps;

placing the clip in intimate proximity to the desired heart tissue;

deforming the clip by applying suitable force to the forceps handles, thus attaching the clip to the atrial or ventricular heart muscle tissue; and attaching the pacer electrodes to each of the channels provided in the outer surface of the V-shaped clip.

Optionally the electrodes may be inserted into the channels prior to attachment.

The method of the present invention is safe both in placement and subsequent removal. It is quick, functional and easy to carry out, and no suturing to the atrium is required. Once the V-shaped clip is placed on the right atrium, unipolar or bipolar pacing wires may be attached and then removed quickly and safely.

The clips of the invention are intended for temporary pacing. At the appropriate time after the clips are inserted and the wires are attached, which could be from about 2 or 3 days later or even weeks or months later, the wires will be removed. The clips remain in place in the patient.

It will thus be seen that the objects set forth above, among those made apparent from the preceding description, are efficiently attained and, since certain changes may be made in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A sutureless clip for use as a temporary pacing device connected to the epicardium of the heart, comprising a generally V-shaped clip having two inner surfaces and two outer surfaces, at least one outer surface having one or more channels each suitable for receiving and engaging an electrode, and the outer surfaces having an insulative coating, wherein the clip is readily deformable to allow for its attachment to heart muscle tissue.

2. The sutureless clip of claim 1, wherein one outer surface of the clip is provided with two channels for receiving and engaging pacing electrodes and an insulative barrier extends between the channels and from the outer surface to the corresponding inner surface.

3. The sutureless clip of claim 1, wherein one or both inner surfaces of said V-shaped clip are textured to provide a greater contact surface area.

4. The sutureless clip of claim 1 which has been fabricated from a physiologically acceptable material selected from the group consisting of platinum, iridium, Elgiloy, pyrolitic, carbon coating, ipanium, graphite platinum and iridium oxide.

5. The sutureless clip of claim 1, wherein each channel is provided with means to engage and retain an electrode.

6. A system for placing sutureless clips which comprises:

a sutureless clip of claim 1, grasping forceps having first and second ends and comprising at the first end a set of jaws designed to accommodate the geometry of a V-shaped clip and, at the second end, an elongated set of grasping handles, which handles operationally engage the set of jaws through and about a rotational axis; and a spring means to maintain the forceps in the open position until force is applied to the handles.

7. A grasping forceps of claim 6 wherein the jaws are also provided with retaining means to hold the V-shaped clip in the open position until force is applied to the forceps handles.

8. A grasping forceps of claim 6 which is fabricated from stainless steel.

9. A method for the attachment of pacing electrodes to the human heart comprising:

inserting a sutureless clip of claim 1 in the retaining end of a grasping forceps;

placing the clip in intimate proximity to a desired portion of the heart;

deforming the clip by applying suitable force to the forceps handles, to attach the clip to heart mucle tissue; and inserting each of one or more pacer electrodes into a channel provided in an outer surface of the clip.

* * * * *